United States Patent [19]

Shimamatsu et al.

[11] 4,217,728
[45] Aug. 19, 1980

[54] APPARATUS FOR CULTIVATING ALGAE

[75] Inventors: Hidenori Shimamatsu, Chiba; Yutaka Tominaga, Ichihara, both of Japan

[73] Assignee: Dainippon Ink & Chemicals Inc., Tokyo, Japan

[21] Appl. No.: 950,042

[22] Filed: Oct. 10, 1978

[30] Foreign Application Priority Data

Oct. 11, 1977 [JP] Japan ................. 52-120913

[51] Int. Cl.² .......................................... A01G 33/00
[52] U.S. Cl. ................................................. 47/1.4
[58] Field of Search ........................................ 47/1.4

[56] References Cited

U.S. PATENT DOCUMENTS

| | | | |
|---|---|---|---|
| 2,732,663 | 1/1956 | Dewey | 47/1.4 |
| 3,385,786 | 5/1968 | Klock | 47/1.4 X |
| 3,462,360 | 8/1969 | McKinney | 47/1.4 X |
| 3,468,057 | 9/1969 | Buisson et al. | 47/1.4 |
| 3,768,200 | 10/1973 | Klock | 47/1.4 |
| 3,839,198 | 10/1974 | Shelef | 47/1.4 X |
| 3,959,923 | 6/1976 | Selke | 47/1.4 |

FOREIGN PATENT DOCUMENTS 3068 2/1966 Japan ........................................ 47/1.4

Primary Examiner—Robert E. Bagwill
Attorney, Agent, or Firm—Sherman & Shalloway

[57] ABSTRACT

A flow rectifying device is provided in a cultivation basin used in the cultivation of algae of the type in which there is a horizontal circulating flow of the cultivation water. The flow rectifying device avoids the formation of puddles or stagnant water and provides for uniform flow of the circulating water as the direction of flow changes at corners of the basin. The flow rectifying means includes a plurality of curved parallel fins for smoothly deflecting the flow of the circulating cultivation water and thereby prevents contamination of the cultivation liquid by preventing algae from being destroyed. The apparatus is particularly useful in cultivating blue-green algae of the genus Spirulina and other aquatic lower algae.

3 Claims, 9 Drawing Figures

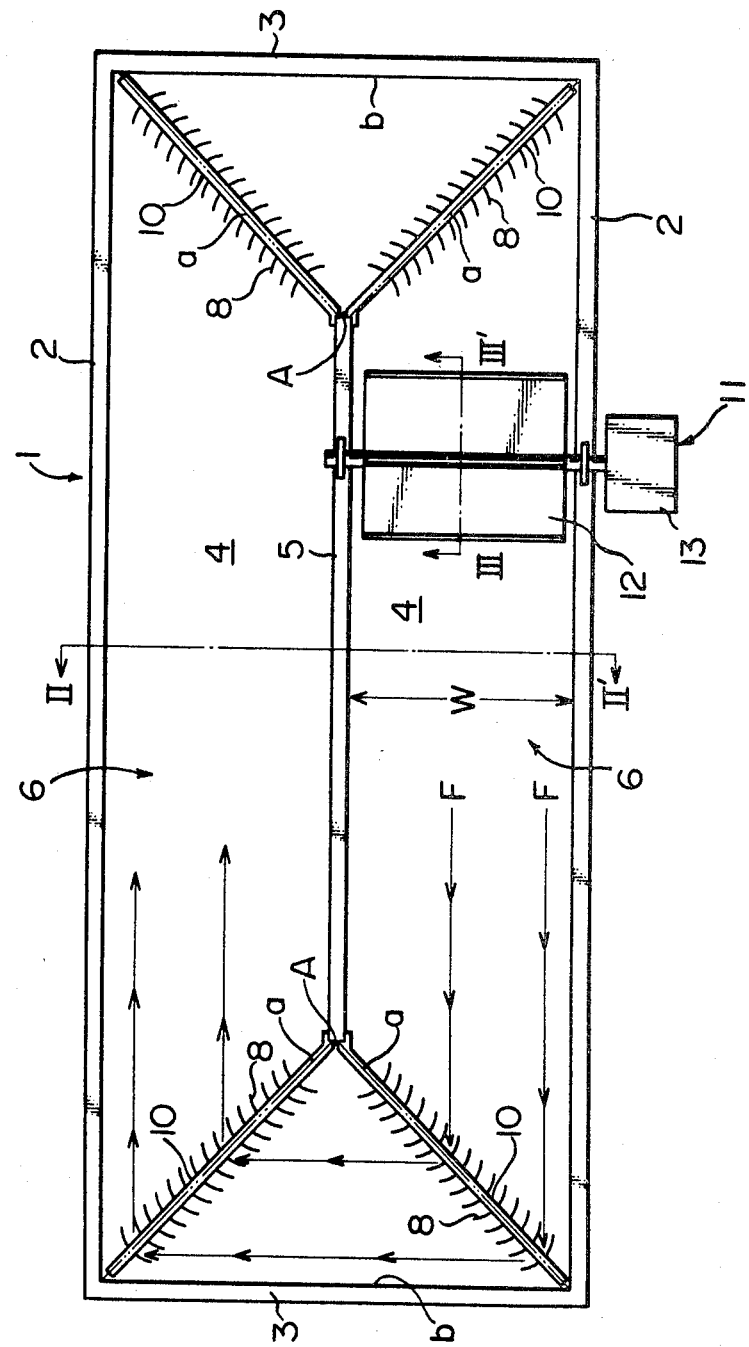

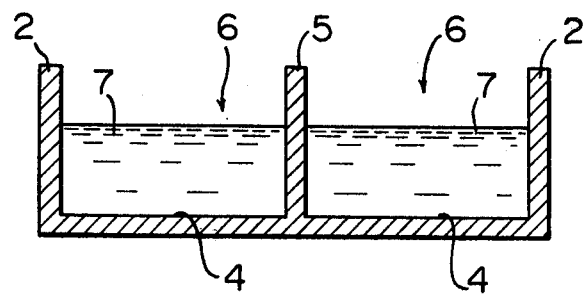
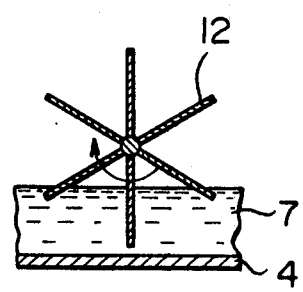
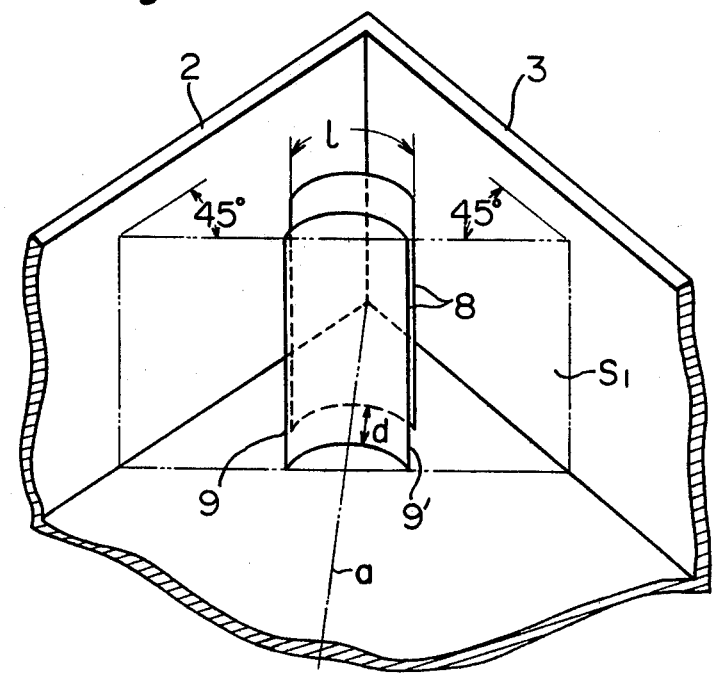

APPARATUS FOR CULTIVATING ALGAE

This invention relates to an apparatus for cultivating blue-green algae of the genus Spirulina and other aquatic lower algae. More specifically, the invention relates to an improvement in a cultivating apparatus used for cultivating algae in a cultivating water which circulates through a deflected flow passage.

Generally, the membranes of aquatic algae are fragile, and multi-celled spiral algae such as blue-green algae of the genus Spirulina are more fragile than single-celled spherical algae such as green algae of the genus Chlorella. Since the damage of the algal membranes means the death of the algae, it is necessary in the cultivation of algae useful as food to stir the entire cultivating water slowly and uniformly so as to impart solar energy effectively and uniformly to each algal cell without damaging it. If puddle or stagnation of water occurs in a basin for cultivating algae which grow by photosynthesis, a supply of light and other nutrient sources becomes insufficient to cause autolysis of algae which leads to putrefaction and death. It would also promote the growth of wild algae, protozoa and other unfavorable organisms.

In rectangular parallelepipedal cultivation basins of the circulating type known heretofore, water which changes in its direction of flow at a corner of the basin does not form a uniform flow, and puddle or stagnation occurs markedly.

A method which is most easily conceivable for gently changing the direction of a circulating cultivation water is to form the flow passage in a cultivation basin in an arcuate shape, or in a shape composed of a combination of an arc and a straight line. Such a basin, however, requires a large floor space for installation, or its cost of construction is high. Particularly, in the latter case, stagnation of the cultivation water cannot be completely prevented.

It is a primary object of this invention to prevent the rupture or stagnation of algae in a deflected flow passage in a cultivation basin, and thereby to prevent contamination of the cultivation liquid by the dead algae or their fragments caused by the rupture or stagnation of the algae.

Another object of this invention is to make the most of a space for installing a cultivation basin.

Still another object of this invention is to provide a cultivation apparatus which is easy and inexpensive to construct.

These objects can be achieved in accordance with this invention by an apparatus for cultivating algae, said apparatus comprising (1) a cultivation basin adapted to permit a horizontal circulating flow of cultivation water and composed of a rectangular bottom wall, two upstanding side walls and two upstanding end walls on the edges of the bottom wall and a partition located intermediate the two side walls and connected only to the bottom wall, (2) a flow driving means for circulating the cultivation water, and (3) a flow rectifying means; said flow rectifying means being composed of a support member and a plurality of parallel fins made of a gently curved rectangular thin plate secured to the support member, each of said fins having such a curved surface that two phantom planes tangent respectively to the opposing two side ends of each fin form an angle of approximately 90°, and said flow rectifying means being provided at a position connecting a corner at which each of said side walls joins each of said end wall to the end portion of said partition so that one phantom plane containing both the two opposing side ends of each fin forms an angle of approximately 45° with respect to said side wall and said end wall.

In spite of the fact that the cultivation basin includes a perpendicularly turning flow passage, the apparatus of this invention can permit a slow and uniform circulation of the entire cultivation water without damaging algal bodies, and does not cause any puddle or stagnation of the flow within the basin. It can therefore prevent the putrefaction of algae and the occurance of wild algae, protozoa, and other unfavorable organisms, to promote efficient sun light reception and photosynthesis, and to produce pure and good quality of algae at high growth rate.

Preferred embodiments of the present invention are described specifically by reference to the accompanying drawings in which:

FIG. 1 is a top plan of an apparatus for cultivating algae in accordance with this invention;

FIG. 2 is a sectional view taken along the line II—II' of FIG. 1;

FIG. 3 is a sectional view taken along the line III—III' of FIG. 1;

FIG. 5 is a perspective view for illustrating the direction of aligning the fins and their relative positions;

Figure 4C:
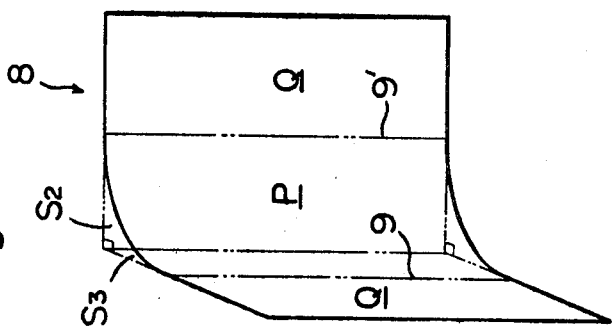
FIG. 4C is a perspective view illustrating a third embodiment of the shaped fin for changing the direction of water flow.

A cultivation basin 1 has a rectangular parallelepipedal contour with an open top which consists of a rectangular bottom wall 4 and two opposing side walls 2 and two opposing end walls 3 which are provided upright on the edges of the bottom wall 4. In the inside of the cultivation basin 1, a circulating flow path 6 through which cultivation water 7 flows is formed by providing a partition 5 located intermediate two side walls 2. The partition 5 is provided upright on a line connecting apexes A of isosceles triangles drawn with a pair of opposing shorter sides of the bottom wall 4 serving as bottom sides b.

Each fin 8 has a curved surface whose cross-sectional shape is an arc with a central angle of approximately 90°, and serves as a water flow turning plate (rectifying plate) for turning the direction of the flow of cultivation water 7 by a certain angle. As shown in FIG. 5, a plurality of fins 8 are aligned at regularly spaced intervals on the equal sides of the triangles with the concave surface of each fin being directed toward apex A. Each fin 8 is provided upright on the bottom wall 4 so that a phantom plane $S_1$ containing both side ends 9 and 9' of its curved surface form an angle of approximately 45° with respect to the side surfaces and the end surfaces. Each fin 8 is fixed to a support member such as a horizontal bar 10 centrally at its top end. A group of fins 8 united by the support member is attachable or detachable to and from the cultivation basin 1.

A flow driving means 11 serves to circulate the cultivation water 7 in a slow uniform flow through the circulating flow path 6, and consists of a flat plate water wheel 12 secured to a shaft between the partition 5 and a side wall 2 and an electric motor equipped with a speed reducer for rotating the flat plate water wheel 12 at a certain low speed.

Now, specific conditions for operating the cultivation apparatus in accordance with this invention will be described.

Preferably, the length of each side wall is at least 10 meters, and the length of each end wall is at least 2 meters. If desired, the side wall may be more than 100 meters in length, and the length of the end wall, at least 20 meters. The depth of cultivation water in the basin is preferably 10 to 30 cm. Hence, the preferred height of the side wall and the end walls is about 50 cm.

The water wheel in the flow driving means consists preferably of a shaft and radially fixed about it, 4 to 10 flat plates each having a length nearly equal to the width of the flow passage. Desirably, the cultivation water should be circulated at an average flow rate of 10 to 60 cm/sec. by this flow driving means. If desired, two or more flat plate water wheels may be provided depending upon the length of the flow passage.

The flow rectifying means should be designed in consideration of such factors as the speed of the water flow, the uniformity of the water flow, the width of the water circulating passage, and the depth of water. For example, when the lengths of each side wall and each end wall are 10 meters and 2 meters respectively, the depth of water is 30 cm, and the water flow is circulated at a rate of 30 cm/sec. by the flat plate water wheel, the water flow rectifying means suitably consists of 16 fins of a shape resulting from dividing a cylinder, 20 cm in radius and 30 cm in length, into four equal sections in the direction of the axis of the cylinder which are attached to a support member at intervals of about 9 cm. Generally, the distance d between two adjacent fins 8 is preferably not more than one-second, more preferably not more than one-third, of the length l of the curved surface of each fin. For example, when the width w of the circulating flow passage is 1 to 10 meters, at least 5 fins 8 are secured to the support member 10, and the distance d between adjacent fins 8 is adjusted to not more than 50 cm.

Figure 4B:
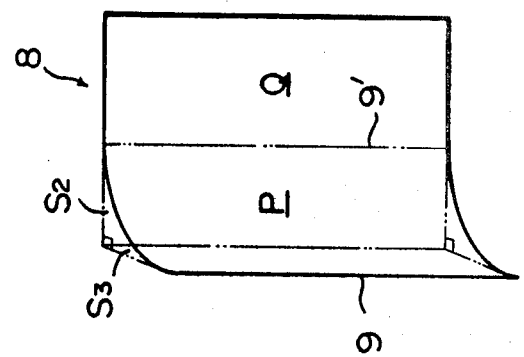
FIG. 4B is a perspective view illustrating another embodiment of the shaped fin for changing the direction of water flow.
Figure 4A:
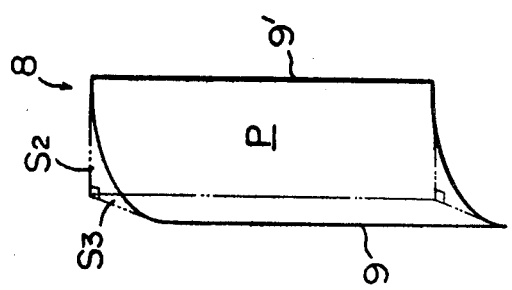
FIG. 4A is a perspective view illustrating one shape of a fin for changing the direction of a water flow.
Figure 6:
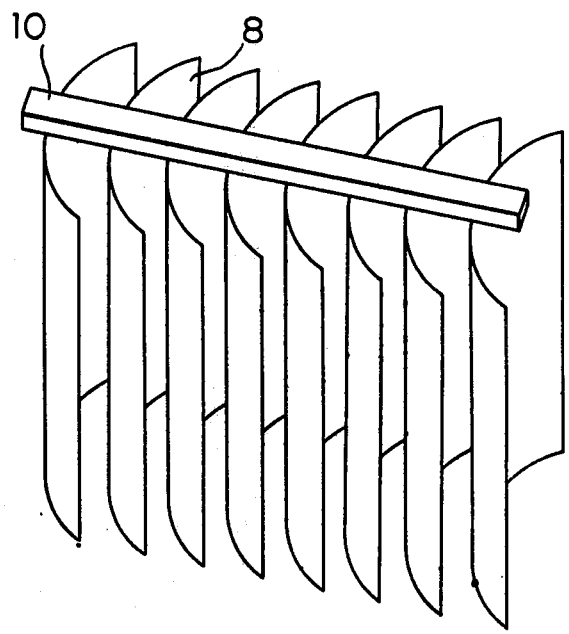
FIG. 6 is a perspective view showing the aligning of the fins.

The concave surface of fin 8 may be a curved surface P of an arcuate cross section as shown in FIG. 4A, or it may be of such a shape that a plane Q projects from one or both of side ends 9 and 9' of the curved surface P of an arcuate cross section tangential to said side end or ends, as shown in FIGS. 4B and 4C. In any case, the fin 8 is so formed that two phantom planes $S_2$ and $S_3$ tangent to the opposing side ends of its curved surface form an angle of approximately 90°. As a result of designing the flow rectifying means in this manner, the fins 8 act to change the direction of the flow of the cultivation water flowing in their vicinity to a nearly perpendicular direction (for example, changing a flow parallel to the side walls to a flow parallel to the end walls).

Since the fins 8 are aligned in the directions and relative positions described above near each corner of the cultivation basin 1, the flowing direction of the cultivation water 1 near each corner is displaced 90° by the fins 8, and it is circulated through the circulating flow passage 6 always as a flow F parallel to the side walls 2 and the end walls 3. The use of the apparatus of this invention therefore does not cause puddle or stagnation near the corners of the basin and at any part of the basin even when the cultivation water is circulated very slowly so as not to damage algae. As a result, the putrefaction of algae and the occurrence of wild aglae, protozoa and other unfavorable organisms are prevented, and effective light reception and photosynthesis are promoted. Thus, pure and high quality algae can be produced at a high rate of growth.

Figure 7:
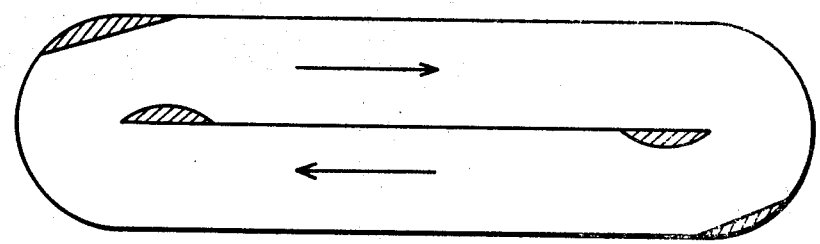
FIG. 7 is a schematic top plan of a conventional cultivation basin.

In contrast, in a known cultivation basin whose ends walls are curved in a semicylindrical shape, the puddle or stagnation of cultivation water cannot be fully removed, and when the cultivation water is circulated in the directions of the arrows in FIG. 7, algae will be putrefied, and wild algae, protozoa and other unfavorable organisms will be formed, at the hatched portions.

Needless to say, auxiliary devices may be fixed to the apparatus of this invention as required. For example, a carbon dioxide supply means may be attached when using the apparatus for the cultivation of algae which well utilize carbon dioxide. The carbon dioxide gas supply means may be of a structure in which its top surface is closed and its bottom surface is opened so that it can retain carbon dioxide gas in the water. Or it may have such a shape as not to cause the disturbance and stagnation of the water flow. It is disposed in a position which does not interfere with the flow driving means and the flow rectifying means, and preferably submerged in the water to avoid shielding of sunlight.

What we claim is:

1. An apparatus for cultivating algae, said apparatus comprising (1) a cultivation basin adapted to permit a horizontal circulating flow of cultivation water and composed of a rectangular bottom wall, two upstanding side walls and two upstanding end walls on the edges of the bottom wall and a partition located intermediate the two side walls and connected only to the bottom wall, (2) a flow driving means for circulating the cultivation water, and (3) a flow rectifying means; said flow rectifying means being composed of a support member and a plurality of parallel fins made of a gently curved rectangular thin plate secured to the support member, each of said fins having such a curved surface that two phantom planes tangent respectively to the opposing two side ends of each fin form an angle of approximately 90°, and said flow rectifying means being provided at a position connecting a corner at which each of said side walls joins each of said end wall to the end portion of said partition so that one phantom plane containing both the two opposing side ends of each fin forms an angle of approximately 45° with respect to said side wall and said end wall.

2. The apparatus of claim 1 wherein each fin is made of a rectangular thin plate which is curved so that it forms an arc corresponding to ¼ of a circle at its cross section.

3. The apparatus of claim 1 or 2 wherein each fin has an extending plane on one or both sides of the curved surface along a phantom plane tangent to the side end of the curved surface.

* * * * *